(12) United States Patent
Gratton et al.

(10) Patent No.: US 8,330,123 B2
(45) Date of Patent: Dec. 11, 2012

(54) SYSTEM AND METHOD FOR DIGITAL PARALLEL FREQUENCY FLUOROMETRY

(75) Inventors: Enrico Gratton, San Clemente, CA (US); Enrico D'Amico, Frascati (IT)

(73) Assignee: I.S.S. (USA), Inc., Champaign, IL (US)

( * ) Notice: Subject to any disclaimer, the term of this patent is extended or adjusted under 35 U.S.C. 154(b) by 328 days.

(21) Appl. No.: 12/695,244

(22) Filed: Jan. 28, 2010

(65) Prior Publication Data

US 2011/0180726 A1  Jul. 28, 2011

(51) Int. Cl.
*G01N 21/64* (2006.01)
(52) U.S. Cl. .................................. 250/458.1; 250/459.1
(58) Field of Classification Search ............... 250/458.1, 250/459.1, 461.1, 461.2
See application file for complete search history.

(56) References Cited

U.S. PATENT DOCUMENTS

| | | | |
|---|---|---|---|
| 4,840,485 A | 6/1989 | Gratton | |
| 4,937,457 A | 6/1990 | Mitchell | |
| 5,151,869 A | 9/1992 | Alcala | |
| 5,212,386 A | 5/1993 | Gratton et al. | |
| 5,213,105 A | 5/1993 | Gratton et al. | |
| 5,255,330 A | 10/1993 | Huynh et al. | |
| 5,257,202 A | 10/1993 | Feddersen et al. | |
| 5,323,010 A | 6/1994 | Gratton et al. | |
| 5,485,530 A | 1/1996 | Lakowicz et al. | |
| 6,317,207 B2 | 11/2001 | French et al. | |
| 6,809,816 B2 | 10/2004 | Sharma | |
| 2006/0017921 A1* | 1/2006 | Baker et al. | 356/317 |
| 2009/0250627 A1* | 10/2009 | Wolleschensky et al. | 250/458.1 |

OTHER PUBLICATIONS

W. Becker et al., Fluorescence Lifetime Imaging by Time-Correlated Single-Photon Counting, Microscopy Research and Technique 63 (2004) 58-66.
R.A. Colyer et al., A Novel Fluorescence Lifetime Imaging System that Optimizes Photon Efficiency, Microscopy Research and Technique 71(2008) 201-213.
J.S. Eid et al., Data acquisition card for fluctuation correlation spectroscopy allowing full access to the detected photon sequence, Rev. of Scientific Instruments 71 (2000) 361-368.
E. Gratton et al., A continuously variable frequency cross-correlation phase fluorometer with picosecond resolution, Biophys J 44(3) (1983) 315-24.
E. Gratton et al., Flourescence lifetime imaging for the two-photon microscope: time-domain and frequency-domain methods, Journal of Biomed. Opt. 8 (2003) 381-390.
K.M. Hanson et al., Two-Photon Fluorescence Lifetime Imaging of the Skin Stratum Corneum pH Gradient, Biophys. J., 83 (2002)1682-1690.

(Continued)

*Primary Examiner* — Constantine Hannaher
(74) *Attorney, Agent, or Firm* — Seyfarth Shaw LLP

(57) ABSTRACT

A system and method is provided for improved fluorescence decay time measurement. A digital heterodyning technique is disclosed in which a photon detector is sampled at a rate slightly faster than a digitally pulsed excitation signal. A resulting cross correlation frequency is low enough to be read by inexpensive electronics such as by a field programmable gate array. Phase information in the signal provides correlation with corresponding photon detections.

20 Claims, 7 Drawing Sheets

OTHER PUBLICATIONS

D.M. Jameson et al., The measurement and analysis of heterogeneous emissions by multifrequency phase and modulation fluorometry, App. Spec. Rev. 20 (1984) 55-106.

G.I. Redford et al., Properties of microfluidic turbulent mixing revealed by fluorescence lifetime imaging, J. Chem. Phys. 123 (2005) 224504. R.D. Spencer et al., Measurements of Subnanosecond Fluorescence Lifetimes with a Cross-correlation Phase Fluorometer, Annals New York Academy of Sciences 158 (1969) 361-376.

X.F. Wang et al., Time-Resolved Fluorescence Microscopy Using Multichannel Photon Counting, Applied Spectroscopy, 44 (1990) 25-30.

PCT International Preliminary Report on Patentability, dated Jul. 31, 2012, 5 pgs.

\* cited by examiner

SYSTEM AND METHOD FOR DIGITAL PARALLEL FREQUENCY FLUOROMETRY

FIELD OF THE INVENTION

The present invention is in the field of analytical chemistry, and particularly relates to fluorescence decay time measurement and frequency domain fluorometry.

BACKGROUND OF THE INVENTION

Measurements of Fluorescence Decay Times

Fluorescence is the light emitted by molecules in solution (or in a solid or gaseous state) following the absorption of radiation. Upon excitation with a short pulse of light of very short duration, the fluorescence emitted by the sample is described by the relationship:

$$I(t) = I_0 \exp^{-t/\tau} \quad [1]$$

where $I_0$ is the intensity of the fluorescence at time $t=0$ and $\tau$ is the time it takes the intensity to decrease to a value $e^{-1}$ its original value. The value $\tau$ is called the "fluorescence decay time".

In a multi-components environment, the fluorescence is described by the relationship:

$$I(\lambda, t) = I_0 \sum_i \alpha_i(\lambda_i) \exp^{-t/\tau_i} \quad [2]$$

where the coefficients $\alpha_i(\lambda_i)$, called the pre-exponential factors and the decay times $\tau_i$ characterize fluorescence decay of the i component of the mixture. These parameters can be related to the fractional contributions, defined as the fraction of the total fluorescence emitted by the i component of the mixture:

$$f_i = \frac{\alpha_i \tau_i}{\sum_i \alpha_i \tau_i} \quad [3]$$

In specific measurement situations the decay time of fluorescence is best described by non-exponential relationships. In any experimental case, devices measuring the fluorescence decay times provide the values $(\alpha_i, \tau_i)$ and any other parameter that describes the fluorescence decay times of each component in a mixture.

Frequency-domain and Time-domain Measurement of Fluorescence Decay Times. The instrumentation for the measurement of fluorescence decays times is broadly classified as belonging to one of two groups, time-domain and frequency-domain techniques.

The time-domain technique uses time correlated single photon counting (TCSPC). An example apparatus that employs time-domain measurement of fluorescence decay times is described in U.S. Pat. No. 6,809,816. Usually, a laser emitting short pulses which repeat with a period slightly longer than the common fluorescence lifetime is used as the excitation light source, although other light sources (LEDs, synchrotron radiation, pulsed lamps) can be utilized as well. At the arrival of each pulse, a high precision timer is triggered which records how much time has passed between the arrival of the excitation pulse and the emitted photon. The precision of the technique is determined by the accuracy of the clock. Either a time-to-amplitude converter (TAC) or a GHz digital clock can be employed.

To interpret the lifetime time information obtained by a TCSPC device, a histogram of such arrival times is built. For a single exponential decay, a curve similar to the curve defined by Equation [1] is collected. The decay time $\tau$ is determined using a minimization technique to fit the experimental data to the theoretical decay model. For multiple exponential decays, a curve similar to the curve defined by Equation [2] is built by the instrument. The decay times of the components are detei wined using a minimization technique to fit the theoretical decay model to the experimental data.

For microscopy applications, the TCSPC acquisition electronics is synchronized to the scanning device (usually galvo-controlled mirrors or piezo-controlled stages), and the histogram acquisition restarts for each pixel of the image. The frequency domain technique was developed to avoid using expensive GHz electronics and TAC. It requires the modulation of the excitation light source and of the light detector. A schematic of the excitation and emission light in frequency-domain spectroscopy. The emission light 102 is phase-shifted and demodulated with respect to the excitation light 104 as shown in FIG. 1. The modulated excitation results in a modulated fluorescence with a phase and modulation which is dependent on the lifetime of the excited fluorophores.

The instruments utilized in frequency domain technique are called multifrequency phase fluorometers (MPF) or, simply, frequency domain fluorometers. When using a MPF to determine the characteristic decay times of the fluorescence, the excitation light source is modulated at a frequency $\omega$. The phase shift $\phi$ and the modulation m are measured. Such measurements are repeated at several different values of the modulation frequency, $\omega$ ranging typically from two or three repetitions for a single exponential decay, to up to twenty-twenty five repetitions for multiple exponential decays. The decay times $\tau_i$ determined using a minimization technique to fit the experimental data.

In the first modern frequency-domain instruments, the light source is modulated at a frequency $\omega$ and the light detector is modulated at a frequency $(\omega + \Delta\omega)$. The two frequencies are provided by phase-locked frequency synthesizers. The approach is also known as "heterodyning". The output signal includes components at the sum ($2\omega$) and the difference ($\Delta\omega$) frequency. The low signal component $\Delta\omega$, called the "cross-correlation frequency", which is typically in the range from 1 Hz to 20 KHz, is utilized to determine the phase shift and the demodulation of the fluorescence.

From the phase and modulation of the $\Delta\omega$ frequency, the phase and the modulation of the fluorescence can be calculated relative to that of a reference lifetime. The lifetime is deduced from the phase and modulation:

$$\tau_P = \frac{1}{\omega} \tan\phi \quad [4]$$

$$\tau_M = \frac{1}{\omega} \sqrt{\frac{1}{m^2} - 1} \quad [5]$$

Multifrequency Phase Fluorometers

An early frequency-domain instrument featured modulation at three fixed frequencies, the highest being 30 MHz. Single exponential decay times of the order of one nanosecond could be measured by the device while complex decays could not be resolved.

In the first multifrequency phase and modulation fluorometers, two phase-locked synthesizers provide modulation to the light source (frequency ω) and to the light detectors (frequency (ω+Δω)) respectively. The output signal at the cross-correlation frequency Δω is measured and utilized to determine the phase shift and the demodulation. In this instrument, the operator selects the modulation frequencies and their number in the range from 1 MHz to 300 MHz. The phase shift and the demodulation are measured for each frequency in a sequential fashion. Embodiments of this instrument are described in U.S. Pat. No. 4,840,485 and U.S. Pat. No. 5,212,386, for example.

The modulation frequency of the excitation light must be in a range that matches the rate of decay of the excited state. For example, if the lifetime of the excited state is about 1 ns, then the best modulation frequency must be around 160 MHz:

$$f = \frac{1}{2\pi\tau} \approx 160 \text{ MHz} \qquad [6]$$

In order to measure the phase and the amplitude of such a very high frequency with precision, a method that first converts the high frequency to low frequency using the heterodyning principle has been used. A measure of the resulting waveform at low frequency is then achieved by using accurate digital methods. The heterodyning has heretofore been achieved by modulating the gain of the detector at a frequency that is slightly different than the light modulation frequency. For example, if the sample is excited with light modulated at 150 MHz, the gain of the detector is modulated with a frequency that differs from 150 MHz by 1000 Hz (as an example). Due to heterodyning, the current produced by the detector contains the sum and the difference of the two frequencies, that is signals at 300,001,000 Hz and the difference at 1000 Hz. A low pass filter separates the low frequency at 1000 Hz from the high frequency component. The low frequency current is then sampled a number of times per period, for example 128 times. The phase shift and the modulation of the frequency at 1000 Hz are obtained from the resulting sample waveform using a fast-Fourier-transform (FFT) technique. The Fourier transform also contains higher frequencies, at 2000 Hz, 3000 Hz and so on up to the half the points in the period, i.e., up to 64 KHz. U.S. Pat. No. 5,212,386 describes an example of such multi-frequency systems.

This approach is commonly used in commercial multifrequency phase and modulation fluorometers (MPF). Examples are the K2 system and Chronos system marketed by ISS Inc. of Champaign, Ill. These instruments utilize both a xenon arc lamp and a continuous wave (cw) laser in conjunction with a Pockels cell, or laser diodes and light emitting diodes, which are modulated directly. Modern MPFs can work with pulsed sources as well such as mode-locked lasers and synchrotron radiation provided they are phase-locked with the synthesizer that modulates the gain of the light detector.

In 1989 a "parallel multifrequency" instrument was described in U.S. Pat. No. 4,937,457 and U.S. Pat. No. 5,257,202. In this instrument, which utilizes a pulsed source at a basic frequency ω, phase shifts and modulation data are collected at the base harmonic ω and at the harmonic 2ω, 3ω, etc., up to about 80 harmonics.

For example, if the light impinging on the sample is modulated at 150 MHz, it contains harmonics at 300 MHz, 450 MHz, 600 MHz and so on. After the mixing with the gain modulated detector, the low frequency signal at 1000 Hz, 2000 Hz, and 3000 Hz etc. represents all the harmonics. After the Fourier transform operation, all the harmonics can be measured in parallel.

Although all the harmonic frequencies are measured in parallel, the mixing scheme obtained modulating the gain of the detector in the parallel multifrequency instrument is very ineffective. In fact, the operation of pulsing the detector gain is equivalent to turning the detector ON for a very brief period, resulting in substantial decrease of the detector efficiency. U.S. Pat. No. 5,257,202 describes this effect and suggests keeping the detector ON for 1/16 of the period, providing about 16 frequencies in parallel. It was demonstrated that this is the optimal duty cycle that maximizes the speed of data acquisition and minimizes the losses arising from turning off the detector. This scheme has been used ever since in the so-called parallel frequency-domain lifetime instruments.

A major advantage of the parallel acquisition method is that the electronic circuits for data collections are always in an ON state, so that there is no drift during the change from one radiofrequency to the other. For example, the collection of data at a single frequency has a long dead time due to waiting for the electronic to stabilize when the frequency is switched. The electronics drifts due to heating are larger at high frequencies. This dead time can be on the order of 1-2 seconds per measurement at each frequency. Since about 16 different frequencies are acquired, and it is necessary to alternate between a sample and a reference to compensate for the drifts, the effective dead time can be as long as 60 s or more. As a consequence the total measurement time is on the order of several minutes.

Instead, when using parallel acquisition of many frequencies as obtained using the harmonic content of high repetition frequency lasers, the dead time suffered by single frequency instruments is strongly reduced since in general only two cycles of data acquisition are used, one for the sample and one for the reference compound. However, a disadvantage of the parallel acquisition mode is that the detector is turned ON only for a fraction of time due to the pulse mixing occurring at the detector. Generally the duty cycle for acquiring 16 frequencies in parallel is about 1/16=6.25%. Therefore what is gained in reducing the dead time is lost in part by the very low duty cycle of the measurement.

Both the serial and the parallel fluorometer require the modulation of the gain of the light detectors, namely modulation of a photomultiplier tube (PMT). The modulation can be either pulsed or sinusoidally modulated, as described in U.S. Pat. No. 6,317,207. In traditional analog frequency domain approaches, the PMTs are driven at a frequency slightly shifted from the frequency of the excitation to result in a slow heterodyned cross-correlation signal. An additional manufacturing problem with this apparatus is that hardware changes must be made to the PMTs voltage divider, which can be quite cumbersome, in order to inject the radio frequency signal. In addition, direct modulation of the PMT reduces the total collection efficiency of those PMTs, the maximum being 50%. Also, some detectors, such as avalanche photodiodes (APD) and Microchannel plates (MCP) are not conducive to direct modulation of the gain. Methods have been devised for applying an external modulation to the signal using a mixer however, the dynamic range is greatly reduced. Also, some detectors, such as avalanche photodiodes (APD) are not conducive to direct modulation of the gain.

Fluorescence Lifetime Imaging Microscopy

Fluorescence spectroscopy has been implemented in microscopy to provide images with a high contrast. Fluorescence lifetime imaging microscopy (FLIM) has been employed to provide important information for various applications, particularly biological applications. For instance, ions concentrations can be obtained by choosing a specific fluorophore that responds to the change in ionic concentration of its surrounding by shifting its spectrum and/or changing its lifetime. Filtering part of the spectrum to observe the intensity of the photons emitted by the fluorophore can be one way to quantify the ionic concentration. Because of the inhomogeneous nature of biological samples, the intensity information is mixed with the concentration of the fluorophore. Alternatively, the exponential decay curve of the fluorescence emission, i.e., the lifetime of the fluorescence has been measured. For example, FLIM was used to interpret the pH value in the uppermost epidermis of human skin, which is not available by simple fluorescence intensity imaging microscopy. Despite the importance of FLIM, existing FLIM devices are cumbersome to integrate with fluorescence intensity imaging microscopy systems. Therefore it is not as widely used as fluorescence intensity imaging microscopy.

As in spectroscopy, the existing FLIM devices are grouped into two categories, time domain devices and frequency domain devices. The time domain devices provide higher resolution for the arrival time of each photon, but also have higher cost. The frequency domain devices are in general unable to resolve picosecond lifetimes, but cost less. The time/frequency domain concepts for FLIM adapt directly from the fluorescence lifetime methods in a cuvette with the addition of microscopy techniques. From a mathematical point of view, the data of each pixel of FLIM is no different from the data from a bulk fluorescence lifetime measurement in a cuvette. A fluorescence lifetime image is an image in which each pixel of the image contains lifetime information for a specific region of space.

In the case of microscopy, the size of a sample and the strength of the signal is miniaturized. The temporal resolution is mostly not restricted by the FLIM devices but by the brightness of the sample. Unlike fluorescence lifetime measurements in the cuvettes, where the number of photons collected can be several millions, a microscopy FLIM applications often measure as few as 100 to 1000 photons to determine the lifetime at a set pixel of an image. For purposes of FLIM, the high temporal resolution of the arrival time of each photon provided by the time domain devices is often not necessary. Frequency-domain instrumentation for tissue spectroscopy has heretofore been developed and used in a tissue oximeter for the absolute determination of oxy- and deoxy-hemoglobin concentration in the blood, for example, such as the OxiplexTS system sold by ISS Inc. of Champaign, Ill. The instrument works at one single modulation frequency at about 110 MHz. While the present instrument is suitable for medical research, it cannot be made portable (for sport medicine applications, for instance) as the power utilized by the electronics is too high for the current available batteries to provide power for a reasonable measurement time.

Digital Frequency-Domain Spectroscopy

In addition to the analog frequency domain fluorescence lifetime techniques described above, the implementation of a digital frequency domain FLIM device has heretofore been described. Just as with analog frequency domain techniques, the laser used in the digital frequency domain FLIM device is modulated. However, in the digital frequency domain FLIM device, instead of modulating the PMT, a flip-flop was added to a Kilohertz (KHz) photon counting device. The flip-flop was wired to the externally synchronized and shifted sampling clock (frequency $\omega+\Delta\omega$) and only outputs the cross-correlated photons when the photons arrive during one half-period of the sampling clock. This digital mixer is an inexpensive circuit and it does not require the modulation of the gain of the detector. However, the mixer operation is obtained by multiplying an input train of pulses corresponding to the photons detected by a square wave, therefore only half of the pulses are counted. It is heretofore known that if two (2) mixing circuits are used that have as input, the same train of pulses, but the opposite sign of the square wave, all the photons can be processed in two separate streams.

The cross-correlated photons are slow enough that the KHz photon counting device can sample them several times during each period to determine their phase and modulation. Then the phase and modulation are analyzed in the same way as if they were acquired by analog frequency domain devices. This technique has been used in certain data acquisition cards such as the Model A506 and A508 cards that are sold by ISS Inc. of Champaign, Ill.

SUMMARY OF THE INVENTION

Illustrative embodiments of the present invention disclose an improved apparatus and a method for measuring and determining multiple decay times of luminescence (fluorescence and phosphorescence) in solid, liquid and gaseous samples. Embodiments can be implemented on a spectrofluorometer and on a multi-channel fluorescence lifetime imaging confocal microscope as well as in virtually any devices conducive to the measurement of the decay times of luminescence. In the following, the word "fluorescence" will be utilized in place of "luminescence" because of its common use in the literature and, unless otherwise specified, should be broadly interpreted to mean fluorescence, phosphorescence and/or luminescence.

The illustrative embodiments of the present invention describe a parallel multifrequency phase fluorometer capable of acquiring all of the photons emitted by the sample and therefore provide high sensitivity and fast data collection. Contrary to standard multifrequency phase and modulation fluorometers, the gain of the light detectors is not modulated by using an external frequency generator. Rather, in the illustrative embodiments, heterodyning is performed digitally thus greatly simplifying the amount of electronics components utilized. Because the inventive embodiments do not require the modulation of the gain and/or the signal, virtually any light detectors (PMT, MCP, APD, photodiode) can be equally utilized.

This invention solves problems inherent to the previous data acquisition cards by using different hardware allowing for the synchronization and a different software algorithm enabling the implementation of the digital parallel principle for the simultaneous acquisition of multiple frequencies. Also, the present invention addresses and fixes problems of previous systems in which corruption of the data occurred when certain first-in-first-out (FIFO) registers saturate. The present invention fulfills the major requirements for full digital parallel acquisition frequency-domain fluorescence lifetime measurements both in cuvettes and the laser scanning microscope. As a result of the present invention, new unanticipated capabilities have emerged that were not heretofore understood.

The digital parallel acquisition scheme presented in the present application provides a digital version of the mixing scheme used in parallel acquisition and, advantageously, samples with 100% duty cycle. In addition, since the embodiments of the present invention use only digital electronics, there is no switching time. Also there is no need to cycle between the sample and the reference. As a consequence of these improvements, the total time of data acquisition for collecting 16 frequencies is reduced form several hundred seconds to about 1 s or less. Since the digital electronics used in the illustrative embodiments of the present invention are very stable, the accuracy of the measurement is increased and the electronic noise is reduced.

The presently disclosed inventive digital parallel acquisition method can be implemented in fairly inexpensive digital electronics. It does not require factory calibration and it does not produce radiofrequency emissions. Moreover, it uses very low power which is an important advantage for the implementation of the technique in portable devices for biomedical, biotechnological and clinical applications. Although the principle of the digital frequency acquisition was previously described, it has not heretofore been applied in the field of parallel frequency-domain data acquisition.

The present invention provides a circuit that performs all the logical operations needed for a parallel-digital frequency-domain instrument. Specifically, embodiments of the invention can be synchronized with lasers that are intrinsically modulated or can generate a frequency signal that is used to amplitude-modulate a laser diode or LED. The signal can also modulate an electro-optical modulator (Pockels cell) or an acousto-optic modulator that, in turn, are used to modulate a continuous wave laser. The information necessary for determining when the data are valid is in the data stream itself so that the synchronization is always properly detected. The circuit can operate using two independent channels or four channels. An internal circuit senses that the FIFO could be saturated and interrupts the input data stream without interfering with the time information. For parallel acquisition, embodiments of the invention use up to 16 harmonic frequencies, limited by the particular chip used (to 320 MHZ). Embodiments can achieve 32 frequencies by using a lower repetition rate (10 MHz instead of 20 MHz). Faster chips are available so that a factor of 2 in the highest frequency may be attainable using these chips. However the current implementation up to 320 MHZ is adequate for most applications. Using the averaging principle of the digital circuit embodiments of the invention can handle very high levels of jitters in detectors, reaching a lifetime precision which is only limited by the total number of photons collected rather than by the width of the window used to determine the timing of the photon.

The present invention includes notable advancements in the field which arise from a profound understanding of the behavior of the digital electronics. The result provides a highly stable circuit, which requires very low power to operate. Embodiments of the invention can be used in portable devices and could have many applications in sensors and in imaging.

Embodiments of the present invention can be used to build a portable tissue spectroscopy that is for smaller and less expensive instruments than previously known frequency domain instruments. Also, the use of multiple modulation frequencies according to the present invention, instead of one modulation frequency, allows for the design of smaller sensors, which are of extreme interest for infant applications and, in general, for the measurement of hemodynamic parameters in restricted areas.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION

In digital heterodyning the cross-correlation frequency $f_{cc}$ is the difference between the sampling frequency $f_s$ utilized to probe the collect the data and the excitation frequency $f_{exc}$ of the light source, that is:

$$f_{cc} = |f_s - f_{exc}| \qquad [7]$$

It is convenient to have for $f_{cc}$ a value that is an integer fraction of the sampling frequency; in an illustrative implementation:

$$f_{cc} = \frac{f_s}{256} \qquad [8]$$

As a result, $$f_s = \frac{256}{255} f_{exc} \qquad [9]$$

That is, if the signals of the excitation light $f_{exc}$ waveform and the signal of the sampling frequency waveform are in phase at time t=0, they return in phase after 256 periods of the sampling frequency waveform. This time is also equal to:

$$T = \frac{1}{f_{cc}} \qquad [10]$$

In other words, given a set sampling frequency $f_s$, the inverse of the cross-correlation frequency $f_{cc}$ is time the sampling window slides through the entire 255 waveforms of the excitation pulses; these correspond to the number of waveforms of the emission response of the sample.

The sampling window is subject to certain requirements in order to count all of the photons emitted by the sample, i.e., to have a 100% duty cycle, and insure that the measurement is performed with precision. In an illustrative embodiment, eight sampling windows are generated, each of pulsewidth Δt. Each sampling window is phase shifted with respect to the previous one by a quantity, in degrees:

$$\Theta = 360 * \Delta t * f_s \quad [11]$$

A fast clock equal to four times the sampling window, or $$f_c = 4 * f_s \quad [12]$$

is also generated in order to perform tagging tasks in the counter, that is to tag incoming photon with the sampling window number which corresponds to their arrival time.

In order to relate the window that recorded the photon arrival to the excitation pulse, it is necessary to know its phase with respect to the excitation pulse. The task is performed by the cross-correlation frequency signal, which activates a counter. It provides a measurement of the relative phase difference between the sampling window and excitation clock frequency. For each photon count, the circuitry provides a value identifying the arrival window $w_a$ and the cross-correlation counter value $P_{cc}$. These parameters are combined into a phase index p as follows:

$$p = 255 - \left[\left(p_{cc} + \frac{256\, w_a}{n_w}\right) \bmod 256\right] \quad [13]$$

Where $n_w$ is the number of windows utilized. The phase index is used to generate the cross-correlation phase histogram, H(p), which is a histogram of the phase indexes for each photon detected.

The intensity image at each pixel is provided by:

$$I = \sum_{p=0}^{n_p - 1} H(p) \quad [14]$$

Other parameters can be calculated and displayed easily at this point.

Figure 1:
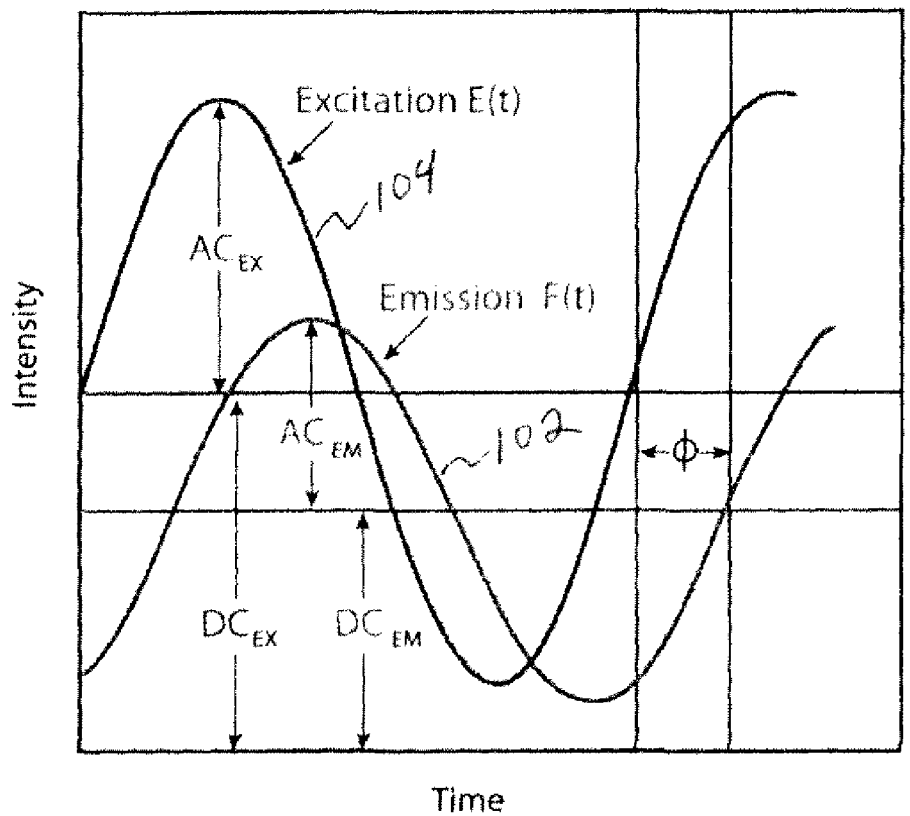
FIG. 1 is a waveform diagram illustrating a phase shift of excitation light relative to emission light as known in the PRIOR ART.
Figure 2:
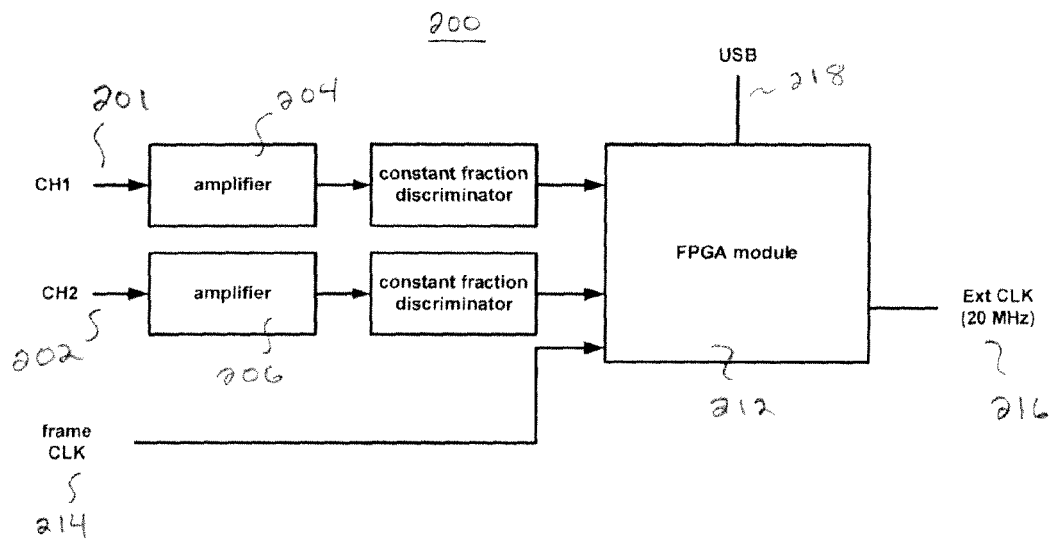
FIG. 2 is a schematic diagram of a dual-channel fluorescence lifetime imaging microscopy (FLIM) unit using photomultiplier tube (PMT) detectors for FLIM applications according to an illustrative embodiment of the invention.

FIG. 2 is a schematic diagram of the dual-channel FLIM unit 200 using PMT detectors for FLIM applications according to an illustrative embodiment of the invention. In FIG. 2, the FastFLIM unit uses two separate photomultiplier tubes, PMTs. A signal from a respective detector goes into channels CH1 201 and CH2 202 and, after signal conditioning (amplification and formatting) by amplifiers 204, 206 and constant fraction discriminators 208, 210, the signal goes into a field-programmable gate array (FPGA) module 212. The FPGA module 212 also received input from a frame clock 214, and an external clock 216 and provides output via USB connections 218.

Figure 3:
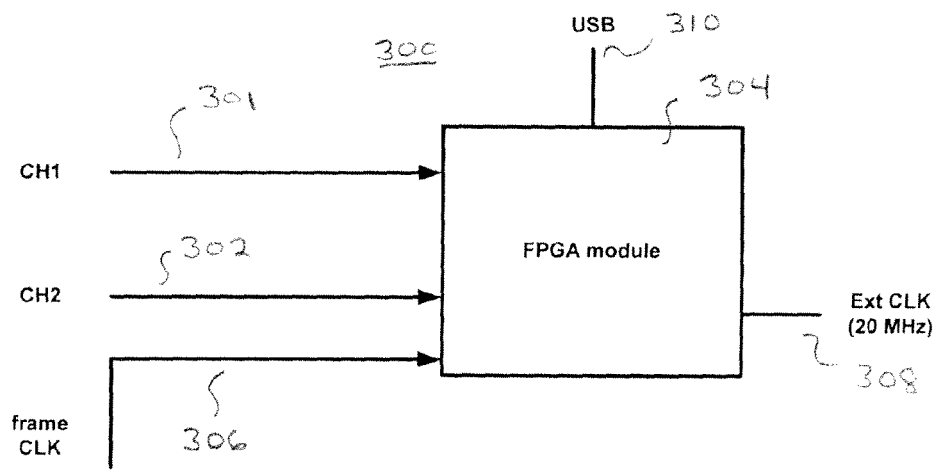
FIG. 3 is a schematic diagram of a dual-channel FLIM unit using single photon counting avalanche photodiode (SPAD) detectors for FLIM applications according to an illustrative embodiment of the invention.

FIG. 3 is a schematic diagram of the dual-channel FLIM unit 300 using single photon counting avalanche photodiode (SPAD) detectors for FLIM applications according to an illustrative embodiment of the invention. In FIG. 3, the FasFLIM unit 300 uses two separate single photon counting avalanche photodiodes, SPADs (not shown). Signals from the respective SPADs are provided as input to channels CH1 301, and CH2 302, of the FPGA Module 304. The FPGA module 304 also receives input from a frame clock 306 and an external clock 308 and provides output via USB connections 310.

In both of the embodiments described with reference to FIG. 2 and FIG. 3, a frame clock 214, 306 is provided to modulate the light source. Data are transferred to the computer using the Universal Serial Bus (USB) port protocol.

In the following example a 2-channel instrument according to an illustrative embodiment of the invention is described. The two-channel digital parallel fluorometer electronics are implemented with scanning coordination on an FPGA chip model Spartan-3E FPGA, Part no. XC3S100E-TQ144 made by Xilinx, Inc. of San Jose, Calif. This chip was chosen for its low-cost, its compactness and the dedicated circuitry for digital clock management (DCM). The DCMs provide a high quality digital clock which can perform fractional frequency adjustments, although, in general, any circuit with sufficiently fast clocking capability and the ability to shift the frequency can be used. To transport the result of the measurement out, the FPGA chip is connected to a USB chip model CY7C60813A, by Cypress Semiconductors of San Jose, Calif. The combination of the two chips is packed by Avnet Electronics Marketing of Phoenix, Ariz. and sold as low cost general purpose evaluation kit.

The FPGA contains two clock managers. When a 20 MHz clock signal is applied as input, two clocks are generated by multiplying the input by a fraction $n_c/m_c$ where $n_c$ and $m_c$ are integers ranging from 1 to 32. In this example, in order to comply with the requirements of Equation [8] above, the values $n_1 n_2 = ^=n_2 = 32$, $m_1 = 17$ and $m_2 = 15$ are used. The frequency is further divided by four in order to generate a clock that is four times the sampling clock. In summary:

$$f_s = \frac{n_1 n_2}{4 m_1 m_2} f_{exc} \quad [15]$$

And hence the cross-correlation frequency is $$f_{cc} = \left| \frac{n_1 n_2}{4 m_1 m_2} - 1 \right| f_{exc} \quad [16]$$

As an example, in one implementation—although other frequencies can be utilized, a frequency $f_{exc} = 20$ MHz is used from which $f_s = 20.07843$ MHz. Hence, the cross-correlation frequency is equal to 78.43 KHz. In a time equal to $$\frac{1}{78.43} = 12.75\ \mu s,$$

the sampling frequency waveform covers 255 waveforms of the excitation signal. Using $f_{exc} = 20$ MHz, the fast clock is generated at $f_c = 80.313$ MHz; the sampling frequency is equal to $f_s = 20.07843$ MHz and the cross-correlation frequency is equal to $f_{cc} = 78.43$ KHz.

A narrow series of pulses is connected to the same signal that carries the photon stream. For each pulse, there is a complementary pulse, so that no photons are ever lost. In principle these pulses can be made very narrow. However, due to the particular electronic chip used in this example, the pulses cannot be made narrower than about 2 ns.

To evaluate how many harmonics can be collected, consider a laser repetition rate of about 30 MHz, which correspond to a period of about 33 ns. If this period is divided into regions of about 2 ns, then about 16 windows are provided in which the photons can be collected.

These 16 windows can produce 15 harmonics. Thus, the digital parallel fluorometer will measure all the harmonic of the 30 MHz signal up to the 15 harmonics, i.e., 300 MHz. These frequencies are adequate for most lifetime measurements both in a spectrofluorometer and in a microscope (FLIM). In fact, a lifetime of 0.5 ns will produce a phase shift of approximately 45 degrees at 300 MHz.

The accuracy of phase measurement using the digital approach according to the present invention is very high. In illustrative embodiments, the phase can be measured with a precision on the order of 0.1 degrees. This precision translates to an error of a few picoseconds only. It is notable that such precision can be obtained with a window of about 2 ns. This is due to the averaging of many photons in the various windows. For the measurement of the time delay of one single photon, the granularity of the lifetime axis is still 2 ns, i.e., the width of the window.

The various examples and illustrative embodiments of the present invention provide for parallel digital acquisition and implementation of the principle using very-low cost digital circuitry with the potential to revolutionize the field of fluorescence measurement and imaging.

A particular problem that can be solved in an implementation of the present invention is the saturation of FIFO requesters used in outputting data which limits the spread of data acquisition. This intrinsic limitation should be understood when considering the operation of the examples. Illustratively assume that a particular example is operating with 16 windows and a laser repetition rate of 20 MHz. Under this condition, each window is 50 ns/16=3.125 ns wide. Only one photon can be detected per window since the circuit has been set to the level one by the detection of the photon. However, the second window becomes active after 3.125 ns and if there is second photon arriving, it can be recorded. However, the pulse length of the detectors is longer than 10 ns, so that the maximum counting rate is actually not limited by the circuit, but it is detector limited. The data recorded in the 16 phases of the period transfers to the data reading register (the FIFO) every time a photon is detected, or a transition at the data enabled line is detected. The granularity of the reading is very small and there is dead time.

However, the output of the FIFO can only be read at the maximum frequency allowed by the USB chip. Although the USB transfer is fast, there is a delay time to process the data transfer request. This delay in typical computers and operating systems is about 3 ms. If during the 3 ms time interval the FIFO fills up, some of the data will be lost. Since the synchronization of the data is more important than the data, the data in is stopped but the data enabled input line is not stopped when the FIFO reaches 80% of its capacity. The FIFO has a capacity of 8192 entries, of which we use approximately 6400 locations. If during a time of 3 ms more than 6400 photons are detected, the circuit saturate. This is equivalent to a sustained rate of about 2 MHz for a period of 2 ms.

This limit could be easily removed using a larger FIFO, however in most applications in microscopy this limit is never reached. If this limit is reached, the laser is attenuated to avoid saturation. Using this scheme, the embodiments are limited by the photon pileup occurring at the detector discriminator. The card per se is not adding pile, but the output of the card suddenly reaches saturation, rather than gradually.

In another example, using an Xilinx 3 board by Xilinx Inc of San Jose, Calif., a series of circuits was produced, all implementing the basic parallel acquisition principle, but for different applications. In this example, the number of lines in the FIFO is 16. In the 16 windows implementation for two independent data channels, 8 lines are used to determine the window number at the time the photon is detected and to determine which of the two channels has detected a photon. One line is used for the data enabled flag and 7 lines are used to determine the macro-clock cycle in which the photon was detected.

Another implementation is used for 4 simultaneous data acquisition channels using the Xilinx 3 board. However, due to the limited number of lines of the FIFO, if two photons have arrived exactly at the same time in more than one channel, the photons are registered, but the timing for that photon can not be determined. This is generally not a problem because this event is rare and the software decides to disregard these particular events.

The different implementations using the Xilinx 3 board put out a narrow pulse at the basic clock frequency which is used to modulate the intensity of lasers diodes or LEDs. For the laser sources that are intrinsically pulsed, a signal is connected to the external clock input of the board so that the card internal operation can be synchronized with the external laser source.

The maximum clock frequency for 16 windows using the Xilinx 3 board was found to be about 20 MHz, which provides harmonic up to 320 MHz. It appears that if higher frequencies are used, the chip misbehaves. This limit is due to the internal limitation of the chip used in the Avnet board rather than due to failure of the present inventive system and method.

Figure 4:
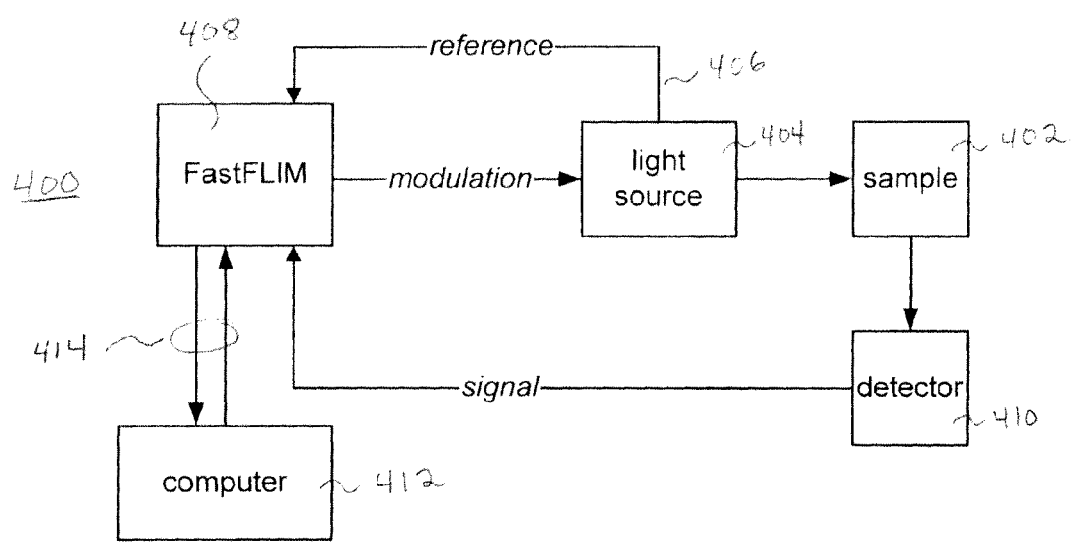
FIG. 4 is a schematic diagram of a parallel multifrequency phase fluorometer according to an illustrative embodiment of the invention.

A parallel multifrequency phase fluorometer embodiment of the invention is described with reference to FIG. 4. The instrument 400 is utilized to determine the decay times of fluorescence in solutions or in solid samples 402. In the illustrative embodiment, the light source 404 is a laser diode. A reference signal 406 is provided in this implementation to the FastFLIM unit 408. The reference signal 406 is not strictly required as the internal clock can be utilized as well. The light detector 410 can be a photomultiplier tube (for instance the type R928 by Hamamatsu, Japan), a microchannel plate detector (for instance, the model R3809U by Hamamatsu, Japan), or an avalanche photodiode (for instance the series SPCM-AQR by EG&G Perkin Elmer, Canada). No modification is required to the voltage divider circuitry of the light detectors. A computer communicates with the Fast FLIM 408 via a USB connector 414, for example.

Figures 5A, 5B:
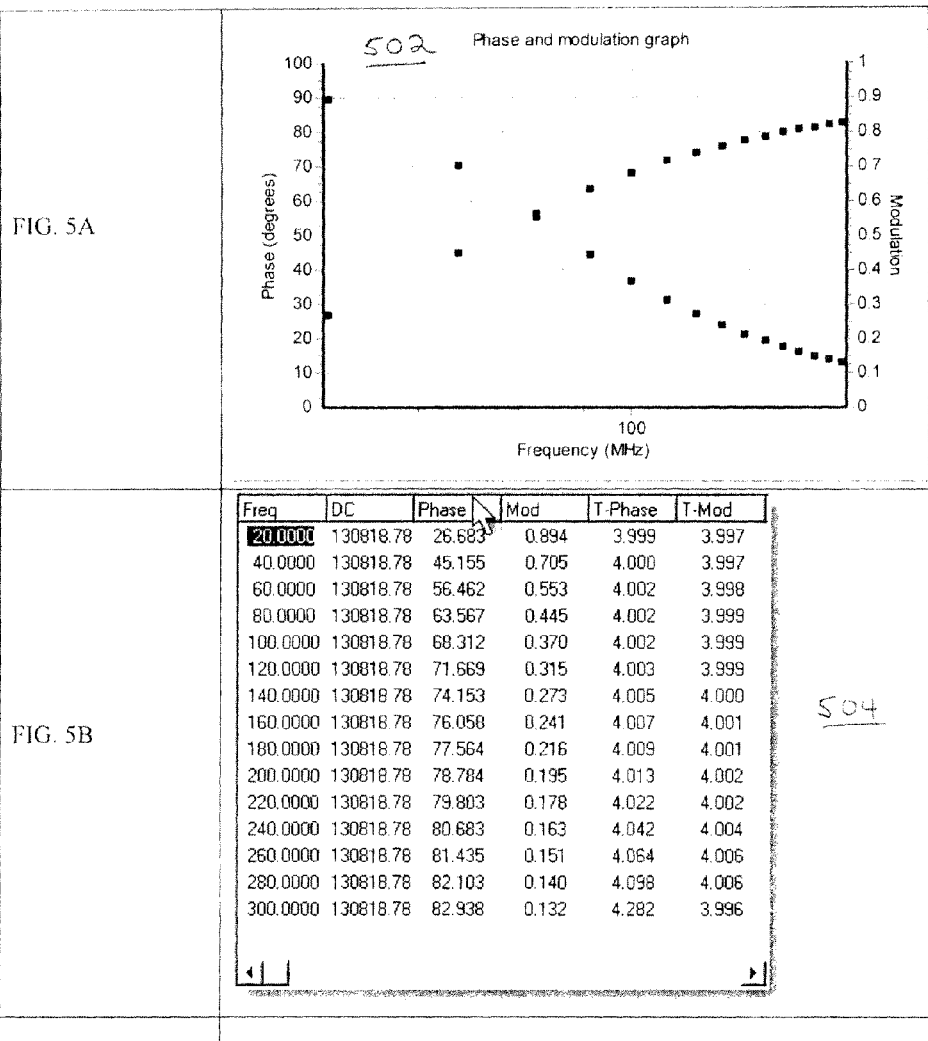
FIG. 5A is a Weber plot describing phase versus frequency data according to an illustrative embodiment of the invention.
FIG. 5B is a table of numerical data showing phase versus frequency data according to an illustrative embodiment of the invention.

FIGS. 5A and 5B provide a graph and table showing a measurement example using the digital parallel acquisition principle. In this example the fluorescence excitation source is a laser operating at 20 MHz so that frequencies up to 300 MHz can be measured. The sample is a solution of Fluorescein at pH 10. Phase and modulation against frequency (Weber plot 502) for Fluorescein is shown in FIG. 5A. Numerical data is shown in FIG. 5B. The excitation source was a laser diode emitting at 473 nm. Lifetime of 4 ns was reported for the sample. The entire data acquisition in this example lasted about 1 s.

The fit of the phase and modulation curves gives a value of the lifetime of 4.00+/−0.01 ns. The expected lifetime of Fluorescein at pH10 is 4.00 ns.

Figure 6:
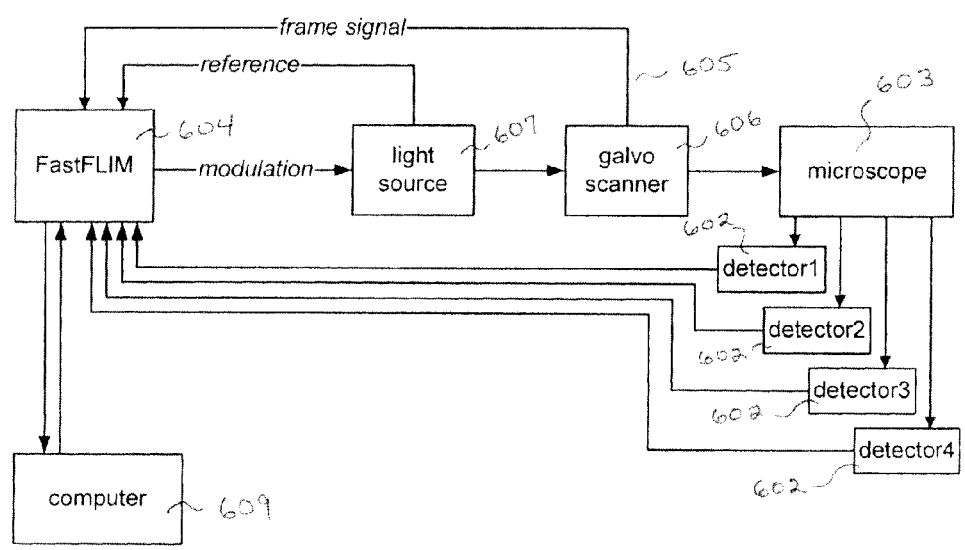
FIG. 6 is a schematic diagram of a multi-channel FL apparatus according to an illustrative embodiment of the invention.

Implementation of the present invention for FLIM measurements is described with reference to FIG. 6. For FLIM applications a 2-channel or multi-channel implementation is feasible. The signals from the light detectors 602 are fed into the FastFLIM electronics 604 which modulate the light source 607 and communicates with computer 609 as described in the previous examples.

To properly implement a circuit that can be synchronized with the scanning operation of a confocal microscope 603, a frame signal 605 from the scanner electronics 606 that accurately reports the instant of time at which the data acquisition in the microscope should start is sent to the FastFLIM unit 604. In this implementation, the card is always collecting data and a flag is added to the data stream which is directly connected to the data valid line of the microscope. Using this approach, no matter what kind of signal the microscope 603 is producing, the data stream record the signal.

The program that determines when data are valid must follow the same logic of the valid data of the microscope 603. This signal could be just a single pulse at the beginning of the frame or a signal that changes and remains the same throughout all the frame. We call this signal the data enabled line. When no photon are present, this signal gets recorded at each period of the clock of the electronic circuit, which is in the 20 MHz range, providing enough synchronization accuracy for pixel dwell times in the range generally used in the microscope (1 to 200 µs).

Data analysis is performed either by determination of the decay times at each pixels or by using a phasor plot approach.

Figure 7:
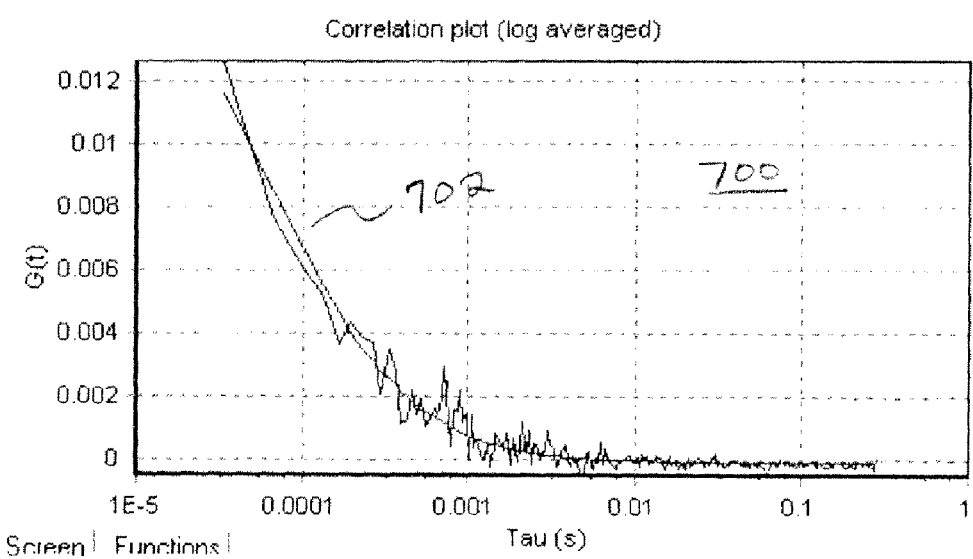
FIG. 7 is an autocorrelation plot of generated using fluorescence fluctuation correlation spectroscopy (FCS) according to an illustrative embodiment of the invention.

In addition to intensity imaging, fluorescence fluctuation correlation spectroscopy (FCS) is another measurement performed on common fluorescence microscopes. The Fast-FLIM circuitry of the present invention can take FCS measurements as well. The setup for performing FCS is the same as FLIM. The cross-correlation clock $f_{cc}$ is used to mark the photon arrival time. FIG. 7 is the autocorrelation plot 700 of a 10 nM fluorescein solution. The curve 702 fits to fluorescein's known diffusion constant.

It is notable to stress that the same electronics can perform both FLIM and FCS measurements according to illustrative embodiments of the present invention.

Figure 8:
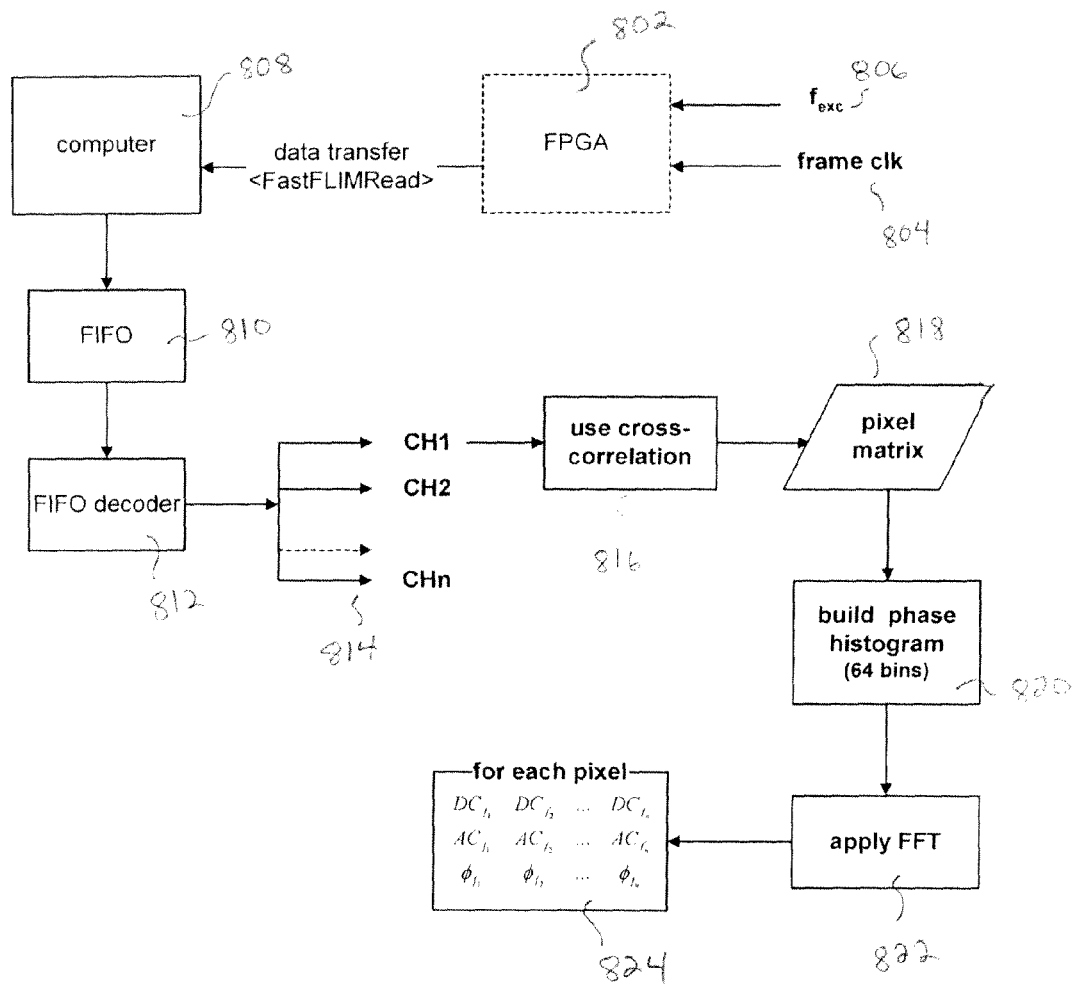
FIG. 8 is a process flow diagram displaying the process of data transfer and the determination of the parameters to be measured by a FLIM apparatus according to an illustrative embodiment of the invention.

FIG. 8 is a flow diagram displaying the process of data transfer and the determination of the measured parameters. An FPGA module 802, such as the FPGA module described with reference to FIGS. 2 and 3, receives a frame clock 804 and an excitation frequency 806. The FPGA module 802 transfers data to a computer 808, via a USB port, for example. The computer 808 outputs data via a FIFO 810 and FIFO decoder 812 to a plurality of channels 814. Data on the plurality of channels 814 is cross correlated 816 to generate a pixel matrix 818. The pixel matrix 818 is used to generate a phase histogram 820. A fast Fourier transform (FFT) 822 is applied to the phase histogram 820 to generate a matrix of values 824 for each pixel. At the end of the process, for each pixel of an image, the following values are provided: DC, the average steady-state intensity; AC, the value of the modulation; and φ, the phase shift of the fluorescence.

These three values are provided for each of the harmonics of the base repetition rate of the laser. That is, when using 20 MHz, values at 40 MHz, 60 MHz, 80 MHz, . . . , 320 MHz are provided. Also, other quantities can be displayed in real time For example, the modulation $$m = \frac{AC}{DC}$$

can be displayed in real time, the decay time calculated using the phase can be displayed in real time, and the decay time calculated using the modulation can be displayed in real time. The parallel multifrequency phase fluorometer process according to the present invention is an instance of the general process described with reference to FIG. 8.

While the invention has been described and illustrated in connection with preferred embodiments, many variations and modifications will be evident to those skilled in the art and may be made without departing from the spirit and scope of the invention. The invention is thus not to be limited to the precise details of methodology or construction set forth above as such variations and modification are intended to be included within the scope of the invention.

What is claimed is:

1. A method of performing parallel muiltifrequency phase fluorometry on a sample, the method comprising:
   irradiating said sample with a pulsed light signal at a predetermined excitation frequency; and
   digitally sampling, by a detector, light emitted by the sample at a predetermined sampling rate selected so that a difference between said sampling rate and said excitation frequency equals a cross correlation frequency that is less than a maximum counting frequency of said detector.

2. The method of claim 1, wherein said sampling rate is externally synchronized and shifted with respect to said excitation frequency.

3. The method of claim 2, wherein said detector comprises a kilohertz photon counting device.

4. The method of claim 1, wherein said cross correlation frequency is an integer fraction of said sampling rate.

5. The method of claim 3, wherein said sampling rate is 256/255 times said excitation frequency.

6. The method of claim 1, wherein said pulsed light is provided by an intrinsically modulated laser.

7. The method of claim 1, wherein said pulsed light is provided by:
   generating a frequency signal; and
   amplitude modulating an emitter selected from the group consisting of a laser diode and a light emitting diode with said frequency signal.

8. The method of claim 1, wherein said pulsed light is provided by:
   generating a frequency signal;
   amplitude modulating an electro-optical modulator or an acousto-optic modulator with said frequency signal to generate a first modulation signal; and
   modulating a continuous wave laser with said first modulation signal.

9. The method of claim 1, wherein said sampling comprises digital heterodyning without modulating gain of said detector.

10. The method of claim 1, wherein said excitation frequency includes a plurality of harmonic frequencies.

11. The method of claim 1, wherein the inverse of said cross correlation frequency, is the time a sampling window samples each waveform of said pulsed light.

12. The method of claim 1, further comprising:
   generating a plurality of sampling windows each with a pulse width [delta-t], wherein each sampling window is phase shifted relative to a previous window in degrees by a quantity 360*delta-t times said sampling rate;
   providing a fast clock equal to four times the sampling rate; and
   determining the phase of a detected photon with respect to a pulse of said pulsed light by relating a sampling window during which a photon was detected to said pulse.

13. The method of claim 12, wherein said determining the phase comprises:
   activating a counter with a signal at said cross correlation frequency; and
   identifying the particular sampling window in which a photon is detected by a corresponding count of said counter.

14. The method of claim 13, further comprising:
   providing, for each count, a first value [Wa] identifying said particular sampling window and a corresponding cross correlation counter value [Pcc];

generating a phase index [P] by combining said first value and said corresponding cross correlation counter value as follows: P=255−[(Pcc+256*Wa/Nw) mod 256], wherein Nw is a number of said plurality of sampling windows.

15. The method of claim 14, further comprising generating a cross correlation phase histogram H(P) of said phase index P for each photon detected.

16. The method according to claim 14, further comprising:
providing an intensity image to an output device, wherein the intensity image [I] at each pixel of the output device is a sum of said histogram H(P) for each photon.

17. The method of claim 1, further comprising:
providing a first in first out (FIFO) data reading register in communication with said detector for transferring data to a computer, said data reading register including a plurality of input lines, a plurality of output lines and at least one data enable line,
preventing saturation of said data reading register by stopping input to said input lines when the register reaches about 80% of its capacity while maintaining input to said data enable line.

18. The method of claim 17, further comprising:
attenuating said pulsed light signal to prevent saturation of said register.

19. A fast fluorescence lifetime imaging apparatus, comprising:
an emitter for irradiating a sample with a pulsed light signal at a predetermined excitation frequency; and
a detector for detecting light emitted by the sample at a predetermined sampling rate selected so that a difference between said sampling rate and said excitation frequency equals a cross correlation frequency that is less than a maximum counting frequency of said detector.

20. The apparatus of claim 19, further comprising:
a field programmable gate array [FPGA] module configured to generate a plurality of sampling windows each with a pulse width [delta-t], wherein each sampling window is phase shifted relative to a previous window in degrees by a quantity 360*delta-t times said sampling rate; and
said FPGA module configured to determine the phase of a detected photon with respect to a pulse of said pulsed light by relating a sampling window during which a photon was detected to said pulse.

* * * * *